United States Patent [19]

Bommer

[11] Patent Number: 5,004,585

[45] Date of Patent: Apr. 2, 1991

[54] COLORIMETRIC DETECTOR TUBE

[75] Inventor: Rainer Bommer, Lübeck, Fed. Rep. of Germany

[73] Assignee: Drägerwerk Aktiengesellschaft, Lübeck, Fed. Rep. of Germany

[21] Appl. No.: 239,318

[22] Filed: Sep. 1, 1988

[30] Foreign Application Priority Data

Sep. 1, 1987 [DE] Fed. Rep. of Germany ....... 3729079

[51] Int. Cl.$^5$ ........................................... G01N 31/22
[52] U.S. Cl. ........................................ 422/58; 422/56; 422/59; 422/60; 422/88; 436/144; 436/167
[58] Field of Search ...................... 422/56, 59, 60, 88, 422/58; 436/144, 167

[56] References Cited

U.S. PATENT DOCUMENTS

| | | | |
|---|---|---|---|
| 3,399,973 | 9/1968 | Grosskopf | 436/144 |
| 3,475,129 | 10/1969 | Peurifoy et al. | 422/60 |
| 3,993,451 | 11/1976 | Verbeck | 422/57 |
| 4,259,287 | 3/1981 | Leichnitz . | |
| 4,482,635 | 11/1984 | Herskovitz et al. | 436/167 |
| 4,680,248 | 7/1987 | Roach | 430/273 |

Primary Examiner—David L. Lacey
Assistant Examiner—Abanti B. Singla
Attorney, Agent, or Firm—Walter Ottesen

[57] ABSTRACT

The invention relates to a colorimetric detector tube having a porous charge. The charge contains an indicating region provided with an indicator ahead of which a pretreatment region is placed which carries a pretreatment substance. The material to be detected form products with the pretreatment substance which lead to a coloration in the indicating region. The detector tube is improved so that its indication is expanded to indicate higher detection concentrations. The detector tube is further improved so that even when the first pretreatment substance is exhausted, a colorimetric indication is made accessible to further quantities of the material to be detected. For this purpose, the charge contained in the tube includes a sequence of several pretreatment regions and indicating regions which alternate one with the other. In another configuration, the charge includes a mixture of pretreatment material and indicating material.

5 Claims, 1 Drawing Sheet

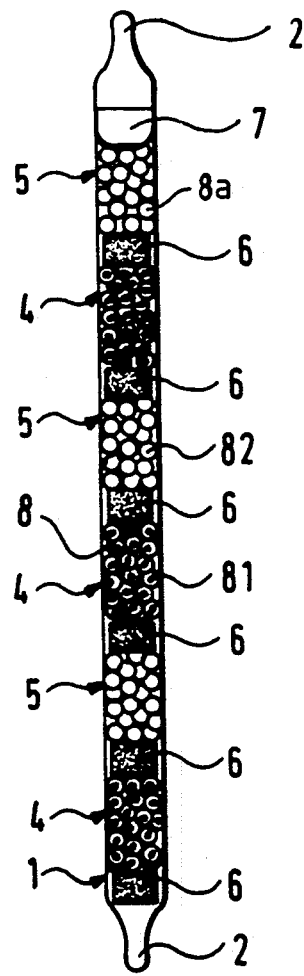
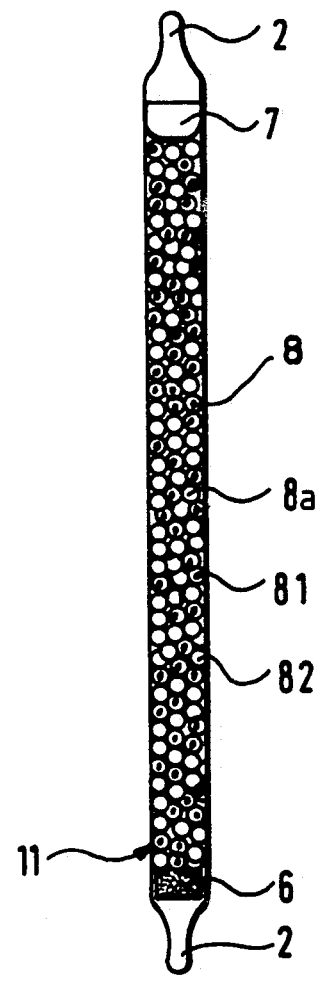

COLORIMETRIC DETECTOR TUBE

FIELD OF THE INVENTION

The invention relates to a colorimetric detector tube having a porous charge which includes an indicating region provided with an indicator. A pretreatment region corresponds to the indicator region and contains a pretreatment substance with which the material to be detected forms products which lead to a coloration in the indicating region.

BACKGROUND OF THE INVENTION

A detector tube of the above-mentioned kind is disclosed in U.S. Pat. No. 4,259,287. In this detecting tube, a pretreatment region is provided for detecting sodium hydroxide and/or calcium oxide aerosols. This pretreatment region is impregnated with $NH_4Cl$. The impregnation forms $NH_3$ from the aerosols which leads to a coloration in the adjacent indicating layer which is impregnated with an acid and bromophenol blue.

A further detector tube for detecting hydrogen includes a pretreatment region which is provided with a palladium catalyzer. The pretreatment region forms water vapor with the hydrogen to be detected and with the atmospheric oxygen. The water vapor leads to a coloration in the indicator layer impregnated with selenium dioxide and sulfuric acid. In this connection, reference may be made to the publication entitled "Detector Tube Handbook" of Drägerwerk AG, Lubeck, May 1985, page 157.

The formation of the products in the pretreatment region occurs quantitatively so that the yield on the one hand is determined by the stoichiometric composition of the pretreatment substance and, on the other hand, from the effectiveness of the catalyzer. If the quantity of the material to be detected exceeds the capacity of the pretreatment substance, the excess portion of the material to be detected passes into the indicating layer without contributing to the coloration there. The consequence is a false measuring result.

On the other hand, the catalyzer which is utilized can be contaminated by an excessive loading of the material to be detected so that its effectiveness diminishes or ceases altogether. As a consequence, the catalyzer allows the material to be detected to pass the pretreatment region unchanged so that a subsequent coloration does not occur in the indicating region. In this way too, the measuring result is falsified.

SUMMARY OF THE INVENTION

It is an object of the invention to improve a colorimetric detector tube of the kind referred to above so that its indicating region is expanded to detect higher concentrations. It is a further object of the invention to provide such a detector tube wherein even after the first pretreatment substance is exhausted, a colorimetric indication is made accessible to the further quantities of the material to be detected.

According to a feature of the invention, the charge in the colorimetric detector tube comprises a sequence of several pretreatment regions and indicator regions which alternate with one another.

After the first pretreatment region is exhausted and the coloration of the first indicating region corresponding thereto is completed, the continued supply of material to be detected then passes into the next pretreatment region in which such products are again formed which lead to a coloration in the next adjacent indicating region. This is an essential advantage of the invention. Should the second pretreatment region also be exhausted, then further next adjacent pretreatment and indicating regions can then bring about a display of the excess of the material to be detected which is still present. The unintentional and often unrecognizable erroneous measurement as a consequence of exhausted pretreatment substances is significantly reduced by the cascade-like sequential arrangement of several pretreatment and indicating regions.

In a simple embodiment of the invention, the charge can be defined by a granular carrier substrate which is impregnated layer by layer with the pretreatment substance. Each two mutually adjacent indicator layers are separated from each other by a pretreatment layer. By means of this sequential arrangement, the coloration display is carried out stepwise in each indicator layer. When the first pretreatment layer is exhausted and the display in the next adjacent first indicator layer no longer changes, the second pretreatment layer takes over and forms the detection products which lead to a coloration in the second adjacent indicator layer. This can be expanded as desired in accordance with the number of further successive layer sequences. The overall indication of the detector tube is then determined by means of an addition of the individual linear colorations in the respective indicator layers.

The individual layer lengths can be adapted to the particular applicational requirements. An increase in the indicating resolution is possible especially by shortening the required layer lengths. It is especially advantageous to produce the charge as a mixture of a granular carrier substrate which is impregnated with the pretreatment substance and with the indicator. In this way, a mixture of a pretreatment region and an indicating region is obtained which leads to an increase in the detection sensitivity. The pretreatment region and the indicating region are thereby distributed over the entire length of the detector tube. The coloration zone then advances in the direction of the throughflow through the detector tube so long as unexhausted granular carrier substrate is still available.

A detector tube having such a mixture has the significant advantage that the detection product which is formed no longer has to flow through a more or less long pretreatment layer in order to reach the indicating layer; instead, the detection product reaches the indicator directly after its formation. The pretreatment substance and the indicator are disposed directly on adjacent granules.

Furthermore, the flow through such a detector tube can be from both ends. No preferred direction for the test gas throughflow is required and errors in handling during use are thereby prevented. Such a detector tube must be simply filled with a mixed charge during manufacture.

A further increase in sensitivity is obtained by providing that the charge comprise a granular carrier substrate which is impregnated with the pretreatment substance as well as with the indicator. Pretreatment of the material to be detected and the colorimetric indication occur at the same location in space so that a precise readout for even low converted quantities of substance is possible.

For detecting hydrogen, the pretreatment substance is preferably palladium and the indicator of the indicating region is a carrier substrate impregnated with crystal violet ($C_{25}H_{30}ClN_3$) and Mg ($ClO_4$)$_2$. For larger quantities of hydrogen, the palladium catalyzer is contaminated by the water which is formed so that its catalyzer action is blocked. The hydrogen penetrating through the first pretreatment region is then converted in the next adjacent palladium catalyzer and is indicated in the indicating region corresponding thereto.

BRIEF DESCRIPTION OF THE DRAWINGS

The invention will now be described with reference to the drawings wherein:

FIG. 1 is a detector tube according to the invention having a plurality of pretreatment and indicator regions on a granular carrier substrate; and, FIG. 2 is a further embodiment of a detector tube according to the invention having a granular charge comprised of a mixture of the carrier substrate with pretreatment substance and indicator.

DESCRIPTION OF THE PREFERRED EMBODIMENTS OF THE INVENTION

FIG. 1 shows a detector tube 1 having a plurality of pretreatment regions 4 and indicator regions 5 arranged sequentially one behind the other between its two ends which can be broken off and in the direction of the through-flow arrow 3. Each pretreatment region 4 is followed by a corresponding indicating region 5 which, in turn, are separated from each other by a porous holding element 6. The indicating region 5 last in the through-flow direction is fixed by means of a resilient pressure piece 7.

The pretreatment substance 81 is placed on a granular carrier substrate 8 and is marked by the black area thereon. The indicator 82 is disposed in the indicating region 5 and is impregnated on the granular carrier substrate 8a and is illustrated by the white granules in the drawing.

FIG. 2 shows a detector tube 11 which contains a granular charge of the carrier substrate 8 between its ends 2. A portion of the charge is provided with the pretreatment substance 81 as shown by the carrier substrate 8 filled out in black and a further portion of the charge is impregnated with the indicator 82 as shown by the white-filled carrier substrate 8.

It is understood that the foregoing description is that of the preferred embodiments of the invention and that various changes and modifications may be made thereto without departing from the spirit and scope of the invention as defined in the appended claims.

What is claimed is:

1. A colorimetric detector tube for detecting hydrogen, the detector tube comprising:
   a tubular housing having first and second openable ends which can be opened to allow a stream of a gas to be detected to pass therethrough;
   a porous charge disposed in said housing between said ends;
   a pretreatment substance arranged on said charge so as to define a plurality of separate pretreatment regions arranged sequentially along the length of said charge so as to be in shaped relationship to each other;
   indicator means arranged on saic charge so as to define a plurality of indicating regions alternating with said pretreatment regions;
   said pretreatment substance in each of said pretreatments regions being selected to coact with the gas to form a product which reacts with said indicator means to form a stepwise coloration in one or more of said indicating regions depending upon the amount of the gas passing into the tube whereby an overall indication of the detector tube is determined by an addition of the individual linear colorations in the respective indicating regions;
   said charge being a granular carrier substrate and said pretreatment substance being impregated into said carrier substrate in said pretreatment regions;
   said indicator means being impregnated into said carrier substrate in said indicating regions; and
   said pretreatment substance being palladium and said indicator means including Mg ($ClO_4$)$_2$.

2. The colorimetric detector tube of claim 1, said indicator means also including a ph-indicator.

3. The colorimetric detector tube of claim 1, said indicator means also including crystal violet $C_{25}H_{30}ClN_3$.

4. A colorimetric detector tube for detecting a gas, the detector tube comprising:
   a tubular housing having first and second openable ends which can be opened to allow a stream of the gas to be detected to pass through said tube in a direction from said first end to said second end;
   a multiplicity of granules defining a charge disposed in said housing between said ends;
   a pretreatment substance impregnated into a first plurality of said granules so as to define a plurality of pretreatment centers arranged along the length of said charge;
   an indicator substance impregnated into a second plurality of said granules so as to define a plurality of indicating centers along the length of said charge;
   said first plurality and said second plurality of granules being thoroughly comingled along the length of said charge; and
   said pretreatment substance on each one of said first plurality of granules being selected to coact with said gas to release a product which migrates directly to adjacent ones of said second plurality of granules to react with said indicator substance to form a coloration zone which advances continuously in said direction to a length depending upon the amount of the gas passing into the tube.

5. A colorimetric detector tube for detecting a gas, the detector tube comprising:
   a tubular housing having first and second openable ends which can be opened to allow a stream of the gas to be detected to pass through said tube in a direction from said first end to said second end;
   a multiplicity of granules defining a charge disposed in said housing between said ends;
   a pretreatment substance impregnated into said granules so as to define a plurality of pretreatment centers disposed in each of said granules and arranged along the length of said charge;
   an indicator substance also impregnated into each of said granules so as to define a plurality of indicating centers along the length of said charge; and
   said pretreatment substance on each one of said granules being selected to coact with said gas to release a product which reacts with said indicator substance on said one granule so that the granules collectively define a coloration zone which advances in said direction in dependence upon the amount of the gas passing into the tube.

* * * * *

UNITED STATES PATENT AND TRADEMARK OFFICE
CERTIFICATE OF CORRECTION

PATENT NO. : 5,004,585
DATED : April 2, 1991
INVENTOR(S) : Rainer Bommer It is certified that error appears in the above-identified patent and that said Letters Patent is hereby corrected as shown below:

On the title page, in the Abstract, line 5: delete "form" and substitute -- forms -- therefor.

In column 3, line 61: delete "shaped" and substitute -- spaced -- therefor.

In column 3, line 63: delete "saic" and substitute -- said -- therefor.

In column 3, line 67: delete "ments" and substitute -- ment -- therefor.

In column 4, line 8: delete "impregated" and substitute -- impregnated -- therefor.

Signed and Sealed this

Twenty-seventh Day of October, 1992

*Attest:*

DOUGLAS B. COMER

*Attesting Officer*   *Acting Commissioner of Patents and Trademarks*